United States Patent [19]

Ryan et al.

[11] Patent Number: 4,998,017

[45] Date of Patent: Mar. 5, 1991

[54] METHOD AND ARRANGEMENT FOR MEASURING THE OPTICAL ABSORPTIONS OF GASEOUS MIXTURES

[76] Inventors: Fredrick M. Ryan, P.O. Box 406, New Alexandria, Pa. 15670; Milton S. Gottlieb, 2310 Marbury Rd., Pittsburgh, Pa. 15221

[21] Appl. No.: 345,863

[22] Filed: May 1, 1989

[51] Int. Cl.$^5$ .......................................... G01N 21/35
[52] U.S. Cl. .................................. 250/343; 250/373; 356/352
[58] Field of Search ...................... 250/343, 373, 338.5; 356/352, 351, 346

[56] References Cited

U.S. PATENT DOCUMENTS

| | | | |
|---|---|---|---|
| 3,939,348 | 2/1976 | Barrett | 250/339 |
| 4,096,388 | 6/1978 | Wong | 250/373 |
| 4,505,550 | 3/1985 | Steinbruegge | 350/372 |
| 4,508,964 | 4/1985 | Gunning, III et al. | 250/201 |
| 4,652,756 | 3/1987 | Ryan et al. | 250/343 |
| 4,732,480 | 3/1988 | Fortunato et al. | 356/346 |

FOREIGN PATENT DOCUMENTS 2555747 5/1985 France .
2555748 5/1985 France .

Primary Examiner—Constantine Hannaher
Attorney, Agent, or Firm—Kinney & Lange

[57] ABSTRACT

A gas analyzer arrangement for detecting the presence or quantity of a gas of interest includes a source of electromagnetic radiation for directing a light beam through a light conditioning device such that the light beam is collimated into a parallel beam of light. The conditioned light beam is then directed through a gas sample cell which contains a sample of the gas of interest. The gas of interest has associated therewith, vibrational rotational absorption lines specific to that gas and which are effective for altering the light beam according to the absorption characteristics thereof. The altered light beam is then directed to a birefringent etalon device which has been sized specifically to match those absorption lines of the gas of interest. An electro-optical modulator device associated with the birefringent etalon modulates the absorption lines between the transmission spectra maxima and a point between the transmission spectra maxima so that an absorption ratio can be utilized to determine the presence or quantity of the gas of interest.

24 Claims, 7 Drawing Sheets

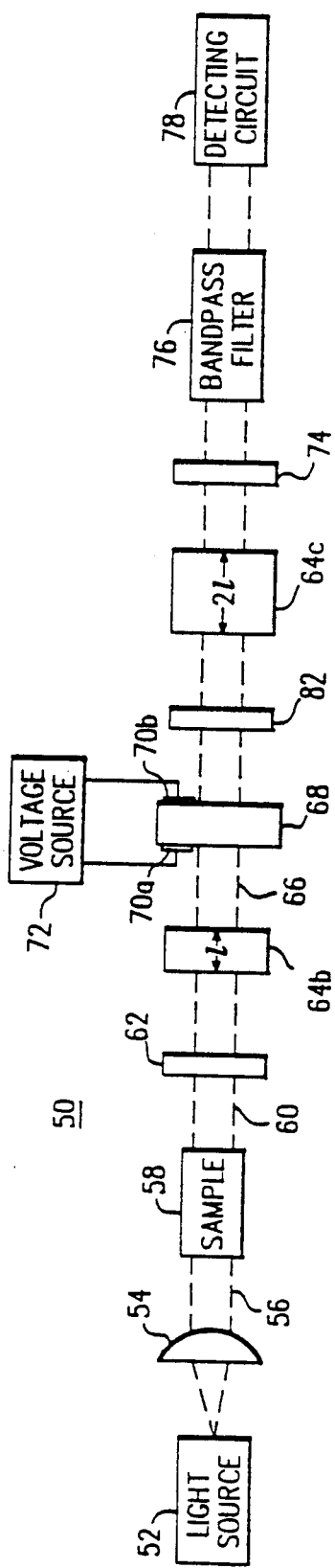
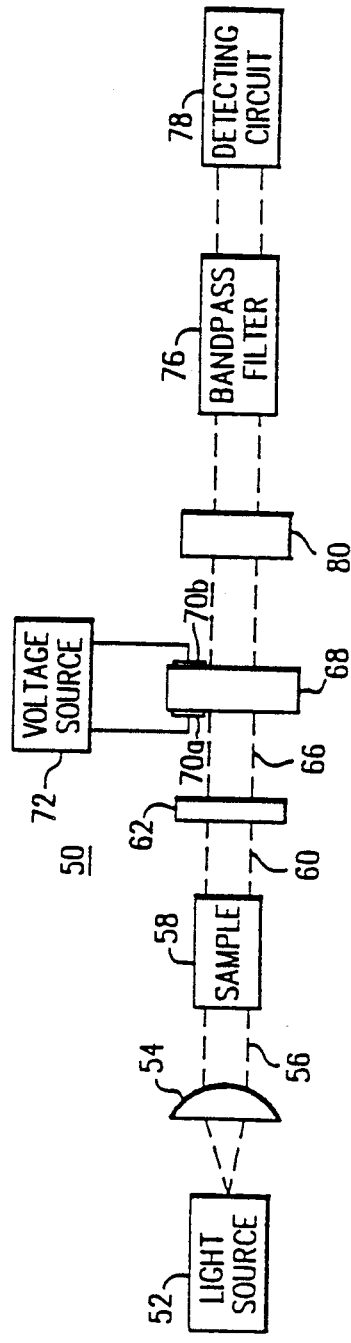
FIG. 4
FIG. 5

FINESSE=A/b

FINESSE=2

FINESSE=4

FINESSE >4

FIG. 7

METHOD AND ARRANGEMENT FOR MEASURING THE OPTICAL ABSORPTIONS OF GASEOUS MIXTURES

CROSS REFERENCE OF RELATED APPLICATION

The present invention is related to material disclosed in the following copending U.S. Patent Application which is assigned to the same assignee as the present application.

U.S. Ser. No. 345,858, "A Method and Apparatus for Remotely and Portably Measuring a Gas of Interest", filed May 1, 1989 by F. M. Ryan and M. S. Gottlieb.

1. Field of the Invention

This invention relates to an improved method and arrangement for measuring the optical absorption properties of various gaseous mixtures. More particularly, this invention relates to such a method and arrangement which utilizes an etalon device and electro-optic modulation techniques to measure the optical absorption characteristics of selected gases.

BACKGROUND OF THE INVENTION

In the field of measuring, detecting and/or analyzing the characteristics of gaseous or liquid mixtures, there's a heavy reliance placed on the evaluation of the absorption spectra that are obtained by use of optical methods. Because of the increased awareness on the part of society as a whole and further because of increased government regulatory activities, this field of monitoring and/or analyzing the various gaseous mixtures that are present in industrial, residential, or commercial environments has been subjected to greater scrutiny and has been the source of increased interest so that more accurate and efficient methods can be developed to detect and subsequently reduce the effects of such gases that may be harmful to persons as well as to the environment. Some of the various gaseous mixtures that are of concern come about as by-products of processes or operations that are essential to society, as for instance, the use of automobiles or the burning of fossil fuels to generate electricity where the concerns are the efficient burning of those hydrocarbon fuels. Consequently, it is obvious that the means for dealing with such gaseous mixtures is not the elimination of the processes that generate them, but instead, in detecting and monitoring these gaseous mixtures and taking steps to contain them so that their effects can be minimized, or in fact neutralized altogether. Examples of some of the gaseous mixtures that are recognized as harmful or where the absence of which may be harmful, are; sulfur dioxide ($SO_2$), ozone ($O_3$), carbon dioxide ($CO_2$), nitric oxide (NO), nitrogen dioxide ($NO_2$), and ammonia ($NH_3$).

An example of an industrial setting where it is necessary to detect these as well as other gaseous mixtures is in the field of monitoring and controlling stack gas pollutants in a combustion control environment. Solid electrolyte compositions which are uniquely responsive to certain gaseous mixtures have been utilized for this type of application, an example of which can be found in U.S. Pat. No. 3,915,830 which issued to A. O. Isenberg on Oct. 28, 1975. In some measurement systems of this type, a sensing electrode which is contacted by the stack gas emissions to be monitored is disposed on one side of the solid electrolyte cell while a reference electrode, which is contacted by reference gas, is disposed on the opposite side of the solid electrolyte cell. An EMF signal is generated which responds to the difference in partial pressure in the gas specie across the electrolyte. This type of approach may require continuous operator monitoring because of the fact that the reference gas may not always be adequately isolated from the stack gas so as to insure that the integrity of the reference gas is maintained to the precise degree necessary. Since the measurement of the stack gas is made relative to the reference gas, it is therefore essential to constantly monitor the reference gas and recalibrate when necessary.

Another approach to the detection and/or measurement of gaseous mixtures is the use of absorption spectroscopic techniques which utilize the fact that, at specific wavelengths of electromagnetic radiation, certain gases exhibit specific absorption characteristics which can be used to identify and quantify particular constituents of that gaseous mixture.

An example of the use of spectrographic techniques for the detection and/or measurement of gaseous mixtures involves the use of a device known as an acousto-optic tunable filter, commonly known as an AOTF. U.S. Pat. No. 3,805,196 which issued to J. D. Feichtner et al. on Apr. 16, 1974 discloses the use of a crystal made of thallium arsenic selenide (TAS) which can be operated in the infrared region of the electromagnetic spectrum to act as an AOTF. Depending on the geometry of the crystal and the RF signal that is used for modulation, the AOTF can be effectively operated in conjunction with the detector which detects the absorption characteristics of the gaseous mixture through which an infrared beam is directed, to achieve the detection of the various gases which are of concern. An example of an application of AOTF technology can be found in U.S. Pat. No. 4,505,550 which issued to K. B. Steinbruegge on Mar. 19, 1985. In this patent, input and output polarizers are coupled to and aligned with the AOTF device so as to attain the precise absorption band center for the gaseous constituents. Another example of an AOTF technology in the field of gaseous mixture detection and monitoring can be found in U.S. Pat. No. 4,652,756 which issued to F. M. Ryan et al. on Mar. 24, 1987. In this patent, the tuning function of an AOTF device is utilized in combination with a source of radiation that produces pulsed light at predetermined wavelengths. A detector, placed across the environment of interest which in this example can be a gas stack, can discriminate between the pulsed light emissions and the steady thermal emissions from the hot gas stack.

Though the use of AOTF devices for the purposes of detecting and/or analyzing gases of interest has been effective in a large number of industrial and commercial applications, the sensitivity of this technology has not reached the level that is now becoming desirable in order to meet requirements of environmental regulations which have been becoming more strict. For instance, if a detection arrangement could be developed that could measure an amount of $SO_2$ in an environment of interest at a level of 10 ppB, such a detection arrangement could easily meet present and proposed environmental regulations. Although there are presently certain types of gas measurement arrangements in existence, which are capable of operating in this range, such arrangements suffer from deficiencies such as an inability to be modified so as to operate for a different gaseous mixture, or where such an arrangement can differentiate gases, it is subject to interference because of the filtering arrangement being used. Specifically it is possible to detect SO₂ at this level with an arrangement utilizing an ultraviolet induced fluorescence technique, however, such an arrangement is limited to the application whereby it is desired to detect and quantify SO₂ only, it is not effective for other gases that may be of interest. Additionally, it is possible to use an ultraviolet absorption technique which can be tailored to suit other gases of interest but such technique uses a filter wheel to achieve the specific bandwidth associated with the particular gas of interest. In this approach, because of the limitation of using a filter wheel, it is necessary to operate in a low rotating frequency range which has the disadvantage of increasing the effect of detector noise. The filter wheel approach has the further disadvantage that it measures the relative amounts of light absorbed in two neighboring wavelength ranges and deduces therefrom, the concentration of the absorbing gas present. This approach is not specific to the desired gas however, so that any other absorbing species at these wavelengths will produce an interfering absorption and hence, an erroneous measurement.

Still another technique utilizes an interferometer, or as it is sometimes referred to in the industry, an etalon, to measure the gaseous mixture constituents through the selective transmission of the periodic spectra associated with the gaseous mixture of interest. An example of such a technique can be found in U.S. Pat. No. 3,939,348 which issued to J. J. Barrett on Feb. 17, 1976. In this patent, a Fabry-Perot interferometer is used to provide a plurality of transmission windows regularly spaced in frequency. Selectively separated periodic spectra which are made up of a plurality of rotational, vibrational infrared absorption lines associated with the gaseous mixture of interest, are transmitted in the form of fringes thereby providing a detectable signal from which a determination of the amount of the particular gas of interest can be made. The Fabry-Perot interferometer which is essential to the operation of this arrangement, provides for a mirror separation which can be adjusted to simultaneously transmit all of the rotational, vibrational infrared absorption lines of a molecular species of the gas of interest. This approach to gaseous mixture measurement and detection has provided an advantage in that the sensitivity achieved has been an advance over existing techniques, however, by relying on a mechanical arrangement for providing the selective separation of the periodic spectra, this approach suffers from certain limitations inherent in the use of a mechanical filtering arrangement. For instance, the accuracy and hence, the sensitivity of this approach is dependent on the ability to accurately align the mirror elements of the Fabry-Perot interferometer to the precise bandwidth desired. Additionally inherent in the operation of such a mechanical arrangement is the limitation that modifying the operating characteristics of this measurement technique requires a cumbersome and time consuming manual operation involving the actual alignment or tuning of the mirror separation and the verification of the results of this alignment.

Another example of the use of an interferometer device for the detection and/or measurement of a particular gas of interest can be found in British Patent No. 2,174,198 issued to G. Fortunato on Oct. 29, 1986. In this patent, rather than using a tunable Fabry-Perot interferometer, a stress tunable birefringent etalon is used to achieve the selective separation of the periodic rotational vibrational infrared absorption spectra associated with the particular gas of interest. The modulation arrangement of this approach achieves the specific bandwidth by use of a photoelastic element which is excited by a piezoelectric ceramic so that the birefringence is variable by compression. French Patents 2,555,747 and 2,555,748 issued on May 31, 1985 to Fortunato et al. also employ interferometric techniques; in Patent No. 2,555,747, a piezoelectric element is used to modulate a luminous beam and to provide temperature compensation and in Patent No. 2,555,748 a rotating polarizer is used as a modulation technique.

SUMMARY OF THE INVENTION

It is therefore an object of the invention to provide an arrangement for detecting and/or measuring a gaseous mixture of interest and to perform such detection or measurement operation using an approach that achieves a high degree of accuracy and sensitivity yet allows for the continued operation with a minimum of adjustment and effort.

With this object in mind, the present invention provides a method and apparatus for measuring the optical absorption characteristics of a particular gas of interest which includes a source of electromagnetic radiation as well as a means for conditioning the electromagnetic radiation so as to be directed through a sample of the gaseous mixture of interest. The present invention also provides a means for electrically modulating the electromagnetic radiation that has bee passed through the gaseous mixture of interest; the modulating means including a birefringent etalon and further having associated therewith, a periodic spacing equal to the periodicity of the absorption lines associated with the gaseous mixture of interest. The modulating means is further effective for applying an electric field to the birefringent etalon such that the periodic transmission spectrum is shifted between spectra which coincide exactly with such absorption lines and spectra which fall between such absorption lines. A detecting means is also provided by the present invention, such detecting means being effective for detecting at least the intensity of such periodic transmission spectra following passage through such gaseous mixture of interest, and determining therefrom at least a measurement indicating an amount of such particular gas of interest.

BRIEF DESCRIPTION OF THE DRAWINGS

The preferred embodiments of the invention will be described, by way of example with reference to accompanying drawings in which;

FIG. 4 is an elevational view partly in block diagram form of a gas analyzing arrangement constructed in accordance with a second alternate embodiment of the invention;

FIG. 5 is an elevational view partly in block diagram form of a gas analyzing arrangement constructed in accordance with a third alternate embodiment of the invention;

DESCRIPTION AND OPERATION

Figure 1:
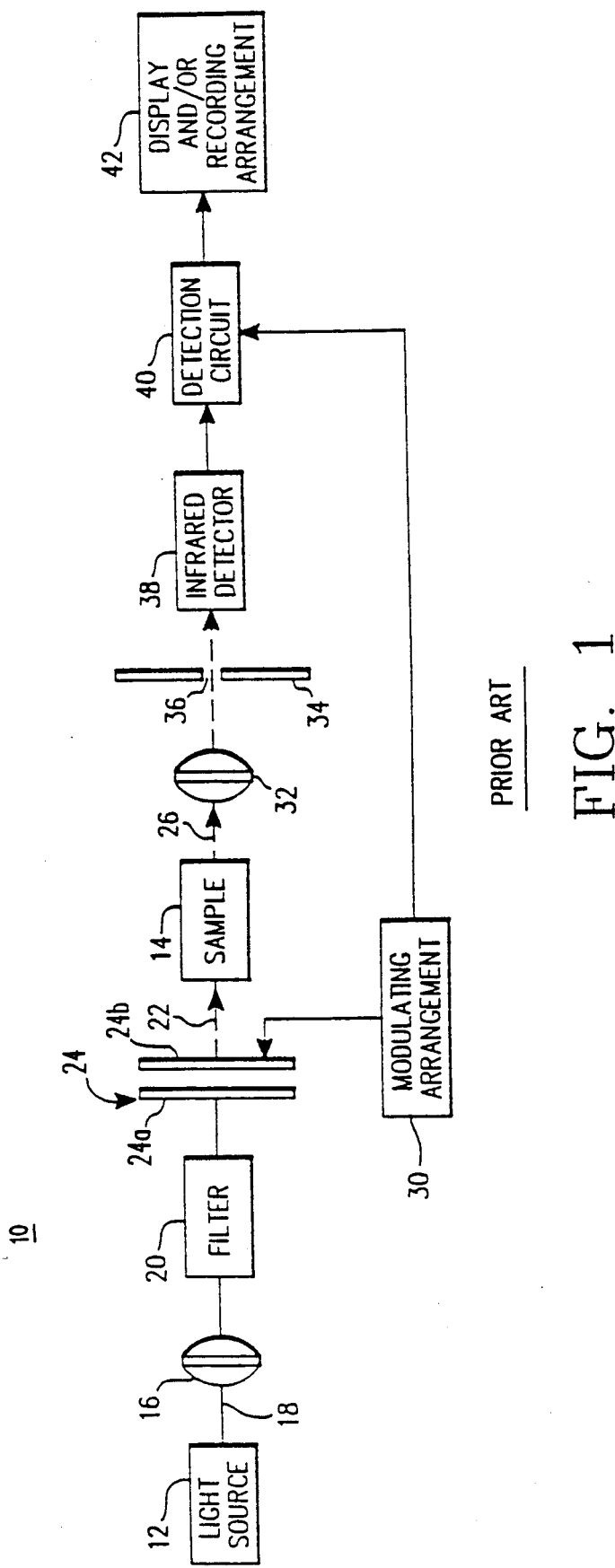
FIG. 1 is an elevational view partly in block diagram form of a gas analyzing arrangement constructed in accordance with the teachings of the prior art.

The present invention will be more readily understood following a description of the prior art illustrated in FIG. 1. This prior art discloses an apparatus for the detection and measurement of various gaseous mixtures based on an evaluation of the selective transmission of the periodic spectra, wherein a Fabry-Perot interferometer 10 is utilized in an overall system to provide a detectable signal from which the concentration of the particular gas specie can be determined. A light source 12 provides a beam of incoherent infrared radiation to a light conditioning arrangement which includes a first lens 16 and a filter 20, which light conditioning arrangement is effective for collecting, collimating and transmitting the beam of radiation to the primary filtering portion of the Fabry-Perot interferometer 10. The Fabry-Perot interferometer 10 provides a plurality of transmission windows regularly spaced in frequency, which frequency spacing between adjacent windows is adjusted to coincide with the absorption spectra of the gas specie to be detected. The light beam 18, after having passed through the interferometer 10 which has coupled thereto, a modulating arrangement 30 effective for providing a shifting of the frequency spacing to approximately one-half the frequency spacing between the adjacent fringes, is transmitted through a sample 14 of the gas specie to be detected. This detectable light signal 26 which emerges from the gas sample 14 is passed through a signal conditioning arrangement consisting of a second lens element 32, a pinhole stop 34 having a pinhole 36 formed therein, and an infrared detector 38.

The second lens element 32 collects and focuses the signal 26 onto the pinhole stop 34 in which the pinhole 36 is formed. The intensity of the signal 26 passing through the pinhole 36 is detected by a infrared detector 38. The infrared detector device 38 operates on the signal 26 and passes it along to a phase sensitive detection circuit 40 for analysis of the signal 26 and a determination of the presence and/or quantity of the particular gas of interest that is present in the sample 14. This determination is made using conventional means as a function of the detected absorption characteristics present in the signal 26. A display or recording arrangement 42 can be placed in series with the phase sensitive detection circuit 40 in a conventional manner.

As discussed hereinabove, the modulating arrangement 30 associated with the second mirror of the interferometer is effective for modulating the phase difference of the detectable signal 26 so as to achieve a precise bandwidth of light, the absorption of which identifies the presence and/or quantity of the gas of interest that is present in the sample 14. The operation of modulating the interferometer 24 involves varying the distance between two mirror segments 24a and 24b which make up the interferometer 24. Inherent in this method of modulation is the limitation typically associated with such a mechanical operation; that is, the accuracy of such a setting is only as reliable as the mechanical linkages used to achieve the desired positioning.

Figure 2:
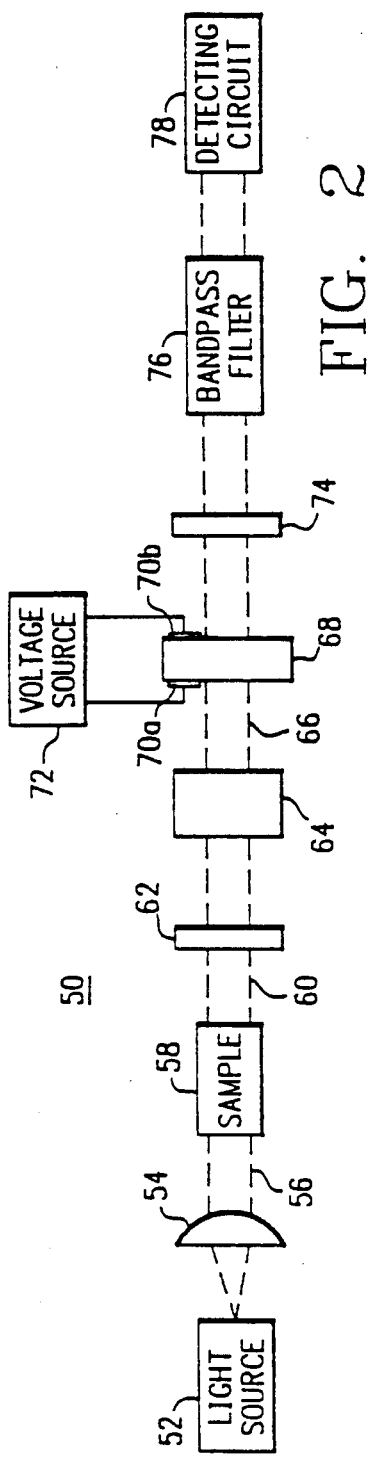
FIG. 2 is an elevational view partly in block diagram form of a gas analyzing arrangement constructed in accordance with the present invention.

In contrast to the mechanical type of modulation arrangement shown in FIG. 1, other prior art teachings have employed still different approaches such as the stress type of modulation used to change the birefringence properties of an etalon device made of a piezoelectric material. As seen in FIG. 2, however, a gas analyzer arrangement shown generally as reference numeral 50 does not utilize either of these types of modulation arrangements; in fact, such an analyzer configuration entirely avoids the use of a mechanical modulation arrangement.

The gas analyzer and/or measurement arrangement 50 shown in FIG. 2 includes a source of electromagnetic radiation 52. In the preferred embodiment of this invention, the source of electromagnetic radiation is an ultraviolet lamp, however, it can be appreciated that other types of light emitting devices could be used as well depending on the wavelength at which the particular gas of interest is absorbed; such other sources of electromagnetic radiation are contemplated as being within the scope of the present invention.

Electromagnetic radiation from the light source 52 is first directed through a light conditioning device such as a collimating lens 54 which is effective for directing the light beam into a parallel stream shown in FIG. 2 as light beam 56. Once conditioned by the collimating lens 54, the light beam 56 is directed to one face of a gas sample cell 58. It should be understood that the gas sample cell 58 is illustrated as a self contained system merely for the purpose of convenience and that, depending on the specific application of the gas measurement and/or analyzer arrangement 50 of the present invention, the means of introducing the gas of interest to the gas sample cell 58 can vary according to the environment in which the gas is found and whether a detection or quantification process is the desired activity. For instance, a gas from a large environment can be channeled to the gas sample cell by a conventional piping arrangement that would channel the gaseous mixture such that it is at equilibrium and at the identical concentration as the gaseous mixture in the larger environment. Additionally, it should be understood that the length of the gas sample cell 58 is a contributing factor to the determination of the quantity of gas that is present; this length will be a known value in the performance of the final calculation done by conventional means and described hereinafter in further detail.

As seen in FIG. 2, the light beam is directed through the gas sample cell 58 along its longitudinal axis thereby exposing the gaseous mixture within the gas sample cell to the light beam 56 so that the optical absorption properties of the gaseous mixture can be utilized to determine either the presence or quantity of the particular gas of interest. Following passage through the gas sample cell 58, the optical properties of the incoming light beam 56 will have been altered such that the light beam 60 which exits the gas sample cell 58 will possess characteristics reflecting the absorption properties of the gas species within the gas sample cell 58. The light beam 60 is directed from the gas sample cell 58 to a first, or input polarizer element 62 which polarizes light beam 60 prior to it being directed to a birefringent etalon device 64. For purposes of discussion relative to FIG. 2, it should be understood that the etalon device 64 is constructed so as to have a length which is specifically associated with the gas of interest; that is, the optical characteristics of the particular etalon used to detect the specific gas are determined by the dimensions of that etalon device.

Figure 6:
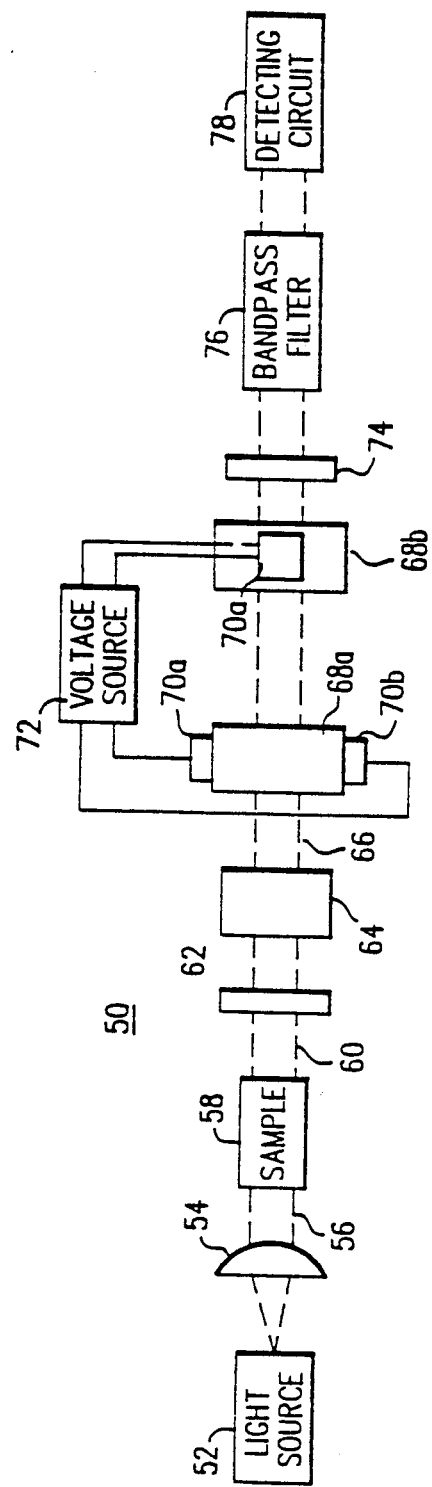
FIG. 6 is an elevational view partly in block diagram form of a gas analyzing arrangement constructed in accordance with a fourth alternate embodiment of the invention.

Etalon devices of the type used herein, can be constructed of any suitable birefringent material such as crystalline quartz; additionally other examples of materials suitable for the construction of etalon devices are: potassium di-hydrogen phosphate (KDP), potassium dideuterium phosphate (KD*P), and ammonium di-hydrogen phosphate (ADP). Furthermore, the material lithium niobate can be used in an application of an etalon device such as is shown in FIG. 6 where the direction of propagation of the light beam is transverse to the application of the electric field used to modulate the birefringent etalon device, such application to be described hereinafter in further detail.

The light beam 60 passes through the birefringent etalon device 64 which has been sized to specifically correlate to the specific gas of interest, and, according to the manner in which the waveshape of light beam 60 relates to the filtering capacity of the etalon device 64, will exit the etalon device 64 as a detectable signal output, which shall be designated light signal 66. This detectable light signal 66 is then passed through to the input surface of an electro-optical modulator device 68. The electro-optical modulator 68 for the preferred embodiment of the invention, is constructed of the material potassium di-deuterium phosphate (KD*P). The electro-optical modulator 68 is operated in the longitudinal electro-optical field configuration; that is, an electric field is applied in the direction of the light propagation. A voltage connected across a pair of thin transparent conducting gold electrodes 70a and 70b can be used to produce this electric field which is responsible for the modulation function. The specified voltage is generated by a conventional voltage generating source shown in FIG. 2 as reference 72.

In order to effectively utilize the properties of the birefringent etalon device 64 in conjunction with the electro-optical modulators 68, it is necessary to practice a technology commonly known as differential absorption spectroscopy. In differential absorption spectroscopy, it is known to measure the absorption at a wavelength in the absorption band of the gas of interest and to compare this absorption to that which is measured at a reference wavelength, the reference wavelength being at a region where the gas of interest exhibits minimal if any absorption characteristics. It is further known that the ratio of these two absorptions produces a value that can be utilized in determining the concentration of the gas of interest. It can be appreciated that the practice of differential absorption spectroscopy is inherently more safe than the use of a non-dispersive absorption spectrometer which utilizes a reference sample cell of the gas of interest as a comparison of the absorption characteristics with the sample of the gas of interest. In this approach, when one is attempting to detect or quantify an amount of a harmful substance such as hydrogen fluoride (HF) or hydrogen chloride (HCL), one must have as a reference material, a sample of that harmful substance.

In the field of differential absorption spectroscopy, it is known that one can achieve the modulation necessary by use of a dispersive device such as a diffraction grading or by means of selected narrow band optical filters. In the present invention, however, the necessary modulation is achieved by applying an electric field to the electro-optical modulator 68 such that the transmission spectra is shifted half the distance between the maxima to achieve what is referred to as the halfwave voltage. In the past, etalon devices have been modulated by means of mechanical arrangements which require that, in order to modify the specific absorption wavelength to recognize a gaseous constituent other than the one originally calibrated, it was necessary to modify the spacing or other mechanical relationship to achieve a different absorption wavelength. With this limitation there would be no flexibility in the use of that particular etalon for the detection or quantification of any gas of interest other than the particular one for which it was constructed. By separating the modulation function from the etalon function, it can be appreciated that different gases of interest can be detected and quantified by merely substituting a different etalon to the overall analyzer arrangement 50 shown in FIG. 2, in other words, there is no need to modify the modulation arrangement.

Following passage through the electro-optical modulator 68, the light signal 66 is directed to an output polarizer 74 and then to a bandpass filtering device 76 which, in cooperation, conditions the light signal to remove unwanted light wave components of the light signal 66. The filtered light signal 66 is then passed on to a detector circuit 78 which determines the presence or quantity of the gas of interest from the gas sample cell 58 using conventional means and the ratio of the absorptions between the periodic spectra, the periodic transmission maxima and the halfway point between the periodic transmission maxima associated with a particular gas of interest.

Figure 3:
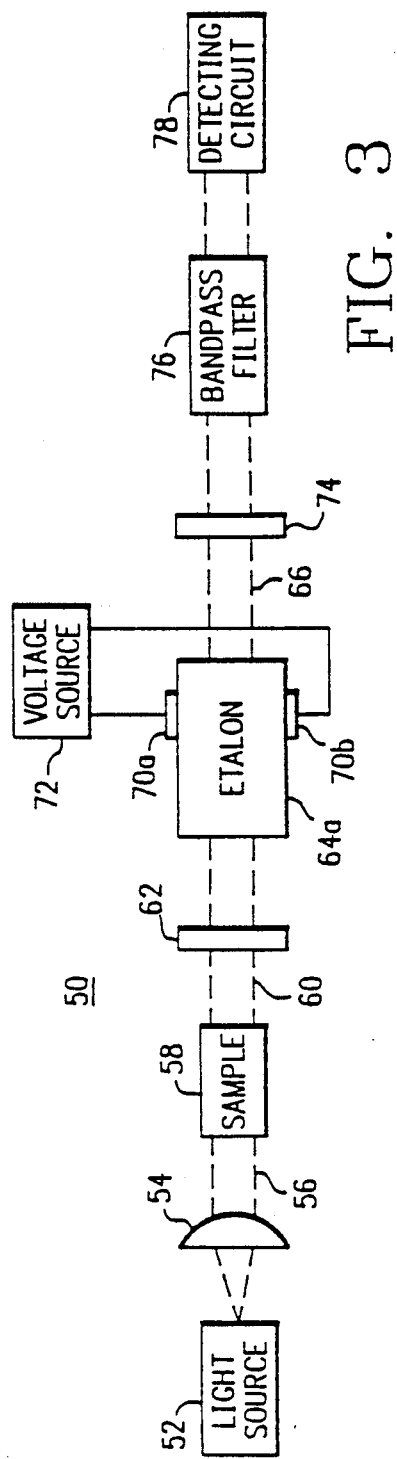
FIG. 3 is an elevational view partly in block diagram form of a gas analyzing arrangement constructed in accordance with an alternate embodiment of the present invention.

As seen in FIG. 3, the construction of the birefringent etalon is shown having the detectable light signal 60 incident to the birefringent etalon device 64 in such a manner that the direction of light propagation is transverse to the direction that the electric field is applied to the electro-optical modulating device 68. Further as shown in FIG. 3, the detectable light signal 60 is shown incident to the surface of the birefringent etalon device 64 which is constructed along crystal planes (001) and (100). The length of the birefringent etalon device 64 is made specifically to match the spacing of the gas of interest in the ultraviolet region. It should be understood that, if it is desired to detect or quantify simple gases which exhibit very narrow absorption lines in the infrared region, for example HCL, the length of the crystal utilized for the birefringent etalon device 64 would be modified accordingly and the light source would have to be changed from an ultraviolet one to an infrared one, both of which modifications are contemplated as being within the scope of the present invention. It should further be appreciated that the prior art analyzers which utilize mechanical arrangements for modulating the etalon device would suffer in their ability to precisely modulate between the periodic transmission maxima associated with gases having narrow absorption lines in the infrared region, and the halfway point between the periodic transmission maxima, a limitation which is not shared by the electro-optical modulation arrangement illustrated herein.

Figure 7A:
FIGS. 7A-F are graphical representations of the absorption spectra of a gas of interest which relates to correlation and anti-correlation spectra with various levels of finesse of the etalon.
Figure 7B:
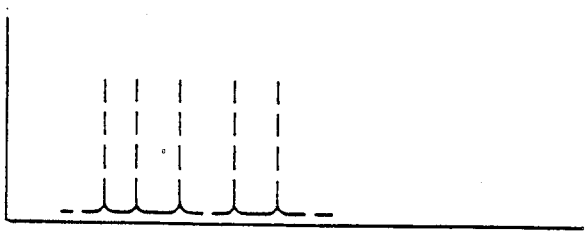
Figure 7C:
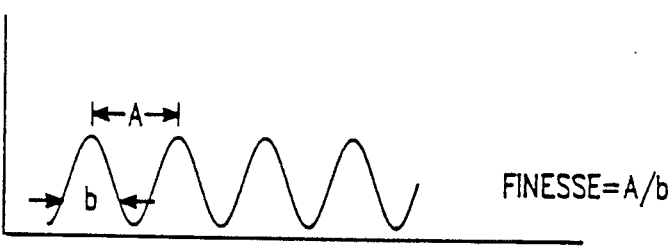
Figure 7D:
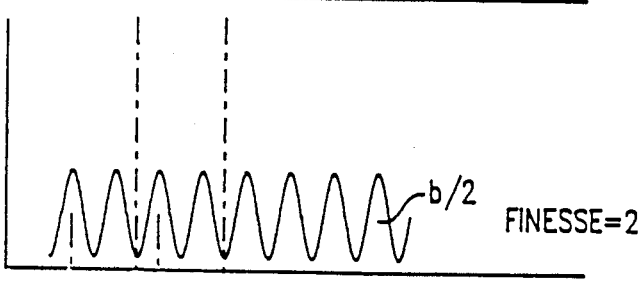
Figure 7E:
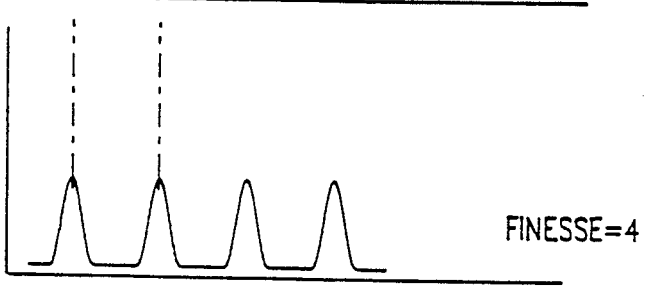

In another embodiment of the present invention, it is desired to achieve a gas measuring and/or analyzing arrangement which can be specifically applied to operate on a gas specie having associated therewith, a very precise narrow bandwidth absorption spectra. The technique of specifically tailoring a substantially identical registration of the absorption characteristics of certain gases, is commonly referred to as a high finesse or increased finesse technique. As seen in FIG. 7A, for gases which exhibit very precise absorption lines, if a filtering arrangement could be provided to substantially correlate with these lines, a more precise measurement essentially immune from interference would result. Accordingly, a gas analyzer arrangement which could provide for such precise correlation between the absorption spectra of the particular gas specie and the filtering capabilities of the interferometer arrangement should also provide a precise tailoring of the anti-correlation waveshape with which the absorption spectra is compared. It should be understood that having the capability to tailor the anti-correlation waveshape in a manner illustrated by the dotted lines of FIG. 7B, will allow for a more accurate determination of the presence and/or quantity of the gas of interest due to the fact that interference from other gases which may have absorption lines in the region under observation, can be avoided. For instance, the anti-correlation lines need not be constructed so as to fall directly between the correlation lines but in fact, because of the ability to precisely specify the location of these lines, they can be disposed near the correlation lines so as to avoid any absorption lines of another gas which may interfere with the accuracy of this desired measurement.

An example of a gas analyzer of this type is illustrated in FIG. 4 where it is shown that a second birefringent etalon 64c is disposed in the light path following the first birefringent etalon 64b, the electro-optical modulator 68, and the polarizer 82. Since the second birefringent etalon 64c has a path length (2l) that is twice that of the first birefringent etalon 64b, it will have a periodic spacing that is one-half ($\frac{1}{2}$) that of the first birefringent etalon 64b. Additionally, by disposing these two etalons 64b and 64c in series, the resulting periodic spacing is such that fewer and narrower absorption lines are achieved as seen in the waveshapes of FIGS. 7C–7F.

Such a gas analyzer arrangement can also be realized by the configuration illustrated in FIG. 5 wherein a compound Fabry-Perot etalon 80 is used in conjunction with the electro-optical modulator 68 to achieve the high finesse gas analyzer arrangement. It should be noted that like elements as are illustrated in the embodiments of FIGS. 2–4 utilize like reference numerals. The compound Fabry-Perot etalon 80 is further shown in FIG. 8B wherein it is shown that the structure is such that the path length l, in conjunction with the index of refraction $n_2$, creates the exact registration of the gas specie of interest.

Figure 7F:
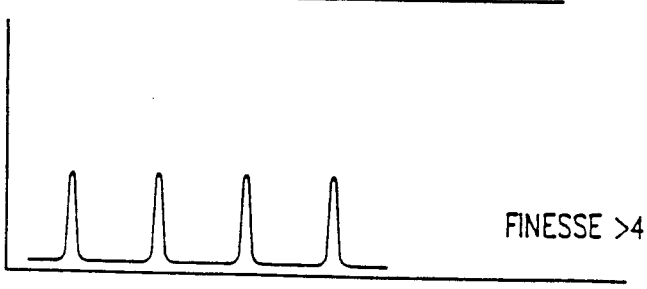

To achieve the necessary indices of refraction that yield the specific correlation and anti-correlation waveshapes, the opposing surfaces formed along the longitudinal axis of the birefringent etalon 80 are coated with a partially reflective surface coating. The amount of reflectivity achieved by the surface coating is determinative of the sharpness of the absorption lines and hence, the high degree of finesse achieved as illustrated in FIG. 7F. Accordingly, it can be appreciated that by varying the amount of surface coating reflectivity, the finesse can be increased or decreased to achieve the sharpness necessary for the anti-correlation waveform to avoid absorbing interference of another gas specie.

Figure 8A:
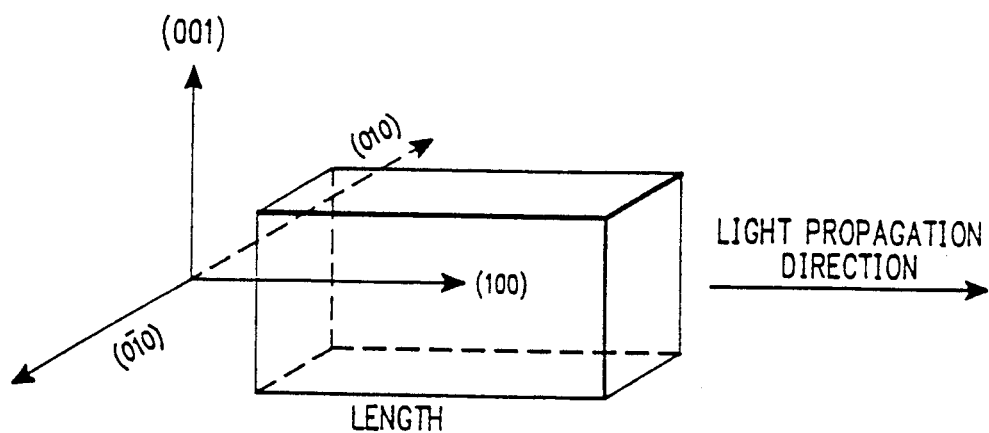
FIG. 8A is an elevational view in section of an etalon device constructed in accordance with the present invention.
Figure 8B:
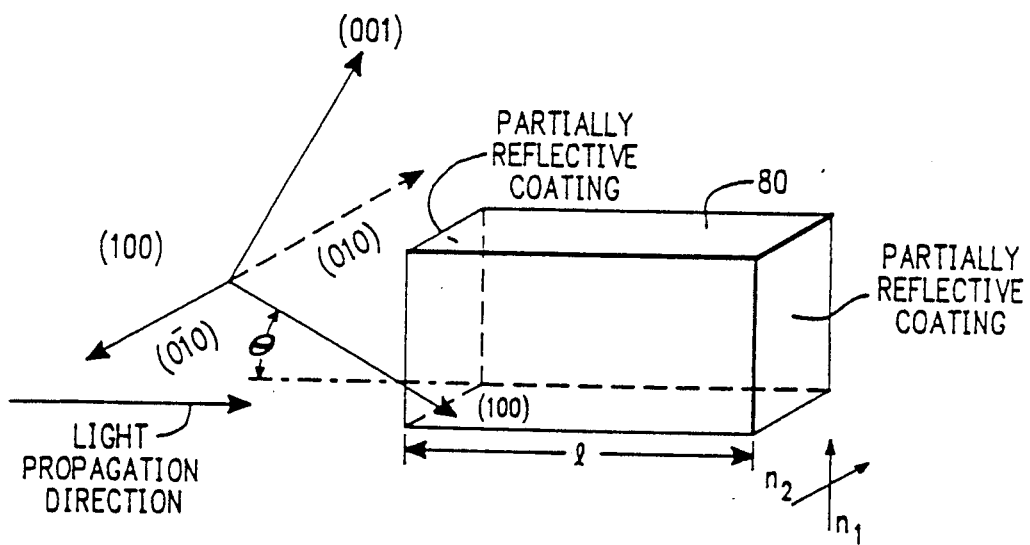
FIG. 8B is an elevational view in section of an etalon device constructed in accordance with the invention as illustrated in FIG. 5.

The index of refraction $n_1$, is determinative of the spacing of the anti-correlation waveshape and can be specified so as to achieve this spacing relative to the correlation waveshape as is necessary to avoid such interference from the absorption spectra of other gas species. The manner by which the selective spacing of the anti-correlation waveform can be achieved is best illustrated in FIG. 8B wherein the optical axii of the compound Fabry-Perot interferometer 80 are illustrated. As illustrated, the index of refraction $n_2$ which is determinative of the correlation waveform frequency spacing, is disposed along the (010) axis and, since this frequency spacing must correlate with the absorption spectra of the gas of interest, this index of refraction $n_2$ must be set and not be variable. The index of refraction $n_1$ however is variable without affecting the disposition of $n_2$ and can be seen to vary from $\theta = 0°$ to $\theta = 90°$ wherein, should $\theta = 90°$, $n_1 = n_2$ and where $\theta = 0°$, $n_1 = n_z$ with $n_z$ being the index of refraction when the optical axis (001) is disposed relative to the axii (100) and (010) as is illustrated in FIG. 8A; that is, when the optical z axis is disposed orthogonal to the plane formed by the optical x and y axii. This selection effectively moves the dotted anti-correlation lines shown in FIG. 7B between the correlation lines to the optimum position to prevent interference and to thereafter set, for the remaining operating life cycle of the gas analyzer arrangement, those indices of refraction once the material structure has been cut.

Yet a further example of a gas analyzing arrangement constructed in accordance with another embodiment of the invention is illustrated in FIG. 6 where the electro-optical modulator 68 is divided into a pair of electro-optical modulators 68a and 68b. For such a configuration, the material used for the modulator can be lithium niobate and the electric field can be applied to each of the modulator segments 68a and 68b in an orthogonal manner with respect to each other and in a direction transverse to the light propagation through the modulator elements 68a and 68b. The effect of such a transverse and orthogonal relationship of the electric field application relative to the modulator elements 68a and 68b and to the direction of light propagation is to provide a cancelling of the birefrigance of the overall modulator configuration 68a and 68b. Of course, it should be understood that to apply the respective electric fields to the modulator elements 68a and 68b in an orthogonal manner requires that the mirrored surfaces of such elements be disposed orthogonal relative to one another.

Figure 9:
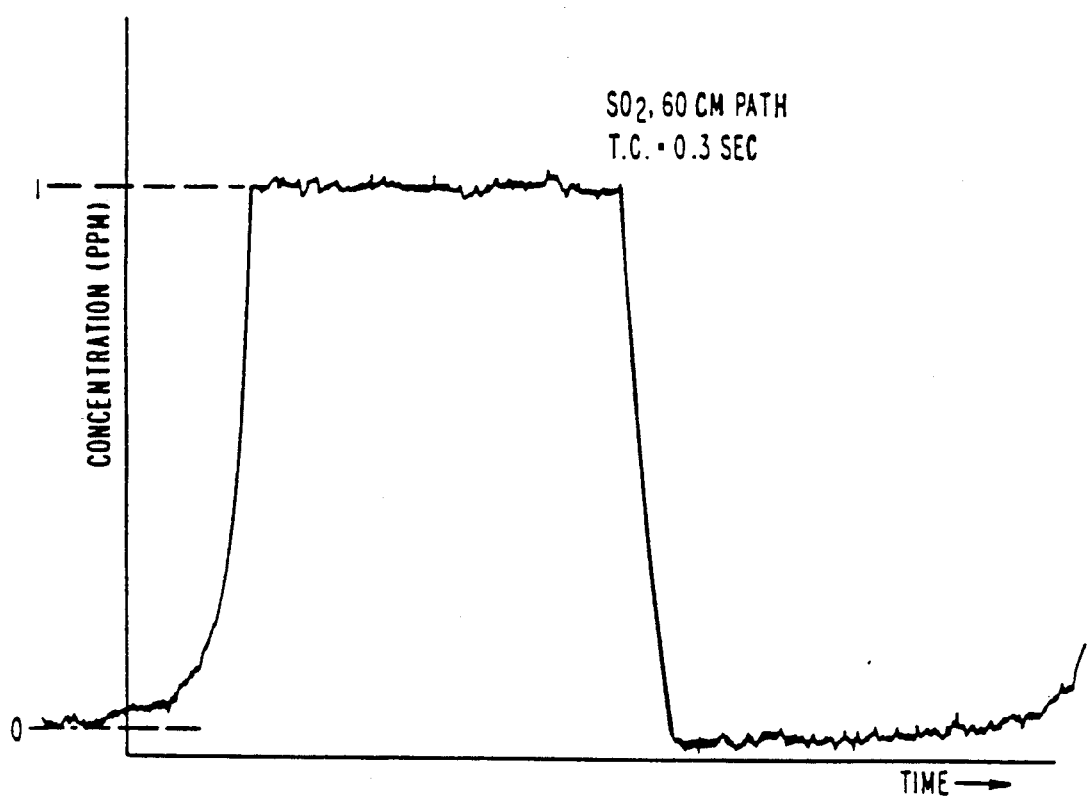
FIG. 9 is a graphical representation of the performance characteristics of the gas analyzing arrangements of the present invention wherein the gas of interest is $SO_2$.

In operation, the gas analyzer arrangement 50 of the present invention will best be understood with reference to FIG. 2 wherein the illustrated interferogram shows the detection of $SO_2$ to a 1 ppM concentration in a gas sample cell 58 having a path length of 60 centimeters. Electromagnetic radiation from the light source 52 is directed to the collimating lens 54 where it is directed into a parallel beam of light referred to as light beam 56. Light beam 56 is then directed to the input face of the gas sample cell 58 which contains the sample of the gas of interest that is to be detected or quantified. Light beam 56, after passing through the gas sample cell 58, emerges therefrom as detectable light signal 60 which differs from light beam 56 because of the fact that the presence of the gas of interest in the gas sample cell has modified the light beam 56 by removing that portion of the ultraviolet spectrum with which its absorption properties can be identified. The detectable light signal 60 is then polarized by input polarizer 62 and directed to the birefringent etalon device 64 which has been sized specifically to correlate to the known absorption band of the gas of interest. By such construction, the free spectral range of the birefringent etalon device 64 is set equal to the vibrational rotational absorption lines of the gas of interest. The etalon lines are then shifted by means of the electro-optical modulator 68 so that such lines alternate between the precise absorption lines of the gas of interest and the point between such absorption lines at which the gas of interest exhibits minimal absorption characteristics. The detectable light signal 66 then passes through the output polarizer 74 and the bandpass filter 76 to the detector circuit 78 which utilizes conventional means to determine the presence or quantity of the gas of interest in the gas sample cell 58 by the ratio of the intensity of the absorption lines of the transmission spectra maxima and the point between the transmission spectra maxima. As further seen in FIG. 9, with a concentration of 1 ppM of $SO_2$ in the gas sample cell 58, the gas analyzer arrangement 50 of the present invention easily distinguishes between the presence or absence of the gas of interest and can also quantify that amount of gas of interest as is present in the gas sample cell 58.

In the alternate embodiments of the gas analyzer arrangement shown in FIGS. 3-6, alternate etalon and modulator configurations are provided with the end result remaining the same; that is, the shifting between the correlation and anti-correlation waveshapes occurs strictly by electrical means and avoids the use of any mechanical modulating arrangement. Additionally, as shown in FIG. 5, the need for an output polarizer has further been eliminated due to the use of the high finesse technique achieved by the compound Fabry-Perot etalon arrangement shown in FIG. 8B.

Although the above discussion describes the preferred embodiments of the invention, it can be appreciated that modifications can be made thereto without departing from the scope of the present invention as set forth in the appended claims.

We claim:

1. An arrangement for measuring a gas of interest by its optical absorption characteristics, comprising:
a source of electromagnetic radiation;
means for conditioning such electromagnetic radiation such that it passes through such gas of interest;
means for electrically modulating such electromagnetic radiation that has passed through such gas of interest, said modulating means including a birefringent etalon having associated therewith, a periodic spacing equal to the periodicity of the absorption lines associated with such gas of interest;
said modulating means being further effective for varying an electrical field applied to said birefringent etalon between first and second predetermined strengths such that the periodic transmission spectrum is shifted between spectra which coincide substantially with such absorption lines and spectra which fall between such absorption lines; and
means for detecting at least the intensity of such periodic transmission spectra following passage through such gas of interest and determining therefrom at least an amount of such gas of interest present.

2. A gas measurement arrangement as set forth in claim 1 wherein said conditioning means includes a collimating element which collimates such electromagnetic radiation into a parallel light beam which can then be directed through such gas of interest.

3. A gas measurement arrangement as set forth in claim 2 further comprising a sample cell in which such gas of interest is disposed, and an input polarizer disposed following said sample cell such that said light beam, after passing through said sample cell, is polarized thereby prior to such light beam entering said birefringent etalon.

4. A gas measurement arrangement as set forth in claim 3 further comprising a second conditioning means for conditioning such light beam after it has passed through said birefringent etalon, said second conditioning means being effective for removing certain known portions of such light beam prior to such light beam being acted upon by said detecting means.

5. A gas measurement arrangement as set forth in claim 4 wherein said second conditioning means includes an output polarizer followed by a band pass filter which, in conjunction, serve to remove fringe and other portions of such light beam which differ from such periodic transmission spectra that coincide with such absorption spectra associated with such gas of interest and such periodic transmission spectra which fall between such absorption spectra.

6. A gas measurement arrangement as set forth in claim 1 wherein said source of electromagnetic radiation can be one of an ultraviolet and an infrared source and is selected according to the spectral wavelength at which the gas of interest exhibits the optimum detection potential determinable as a function of the periodicity of the absorption lines associated thereby.

7. A gas measurement arrangement as set forth in claim 1 wherein said birefringent etalon is constructed of a material having a high electro-optical coefficient whereby, with such electric field applied thereto, said birefringent etalon is simultaneously effective for operation as a filter specifically responsive to such periodic transmission spectra, and as a modulator which, when such electric field is applied, allows such shifting of such periodic transmission spectra between such spectra which coincides with such absorption lines and such spectra which falls between such absorption lines.

8. A gas measurement arrangement as set forth in claim 1 wherein said birefringent etalon is sized so as to achieve a filtering capability specifically responsive to such periodic transmission spectra associated with such absorption lines indicative of such gas of interest, and wherein said modulating means further includes an electro-optical modulator element constructed of a material having a high electro-optical coefficient.

9. A gas measurement arrangement as set forth in claim 8 wherein said birefringent etalon is constructed separately and distinctly from said electro-optical modulator such that, such periodic transmission spectra can be selectively altered to provide detection of an alternate gas of interest by substitution of an alternate sized birefringent etalon, such substitution of said birefringent etalon being done independent of said electro-optical modulator.

10. A gas measuring arrangement as set forth in claim 1 wherein said modulating means includes first and second electro-optical modulator elements disposed orthogonal to one another so that such electric field can be applied thereto in an orthogonal relationship thereby cancelling the birefrigance properties of said first and second modulator elements.

11. A gas measuring arrangement as set forth in claim 2 wherein said collimating element can be one of a collimating lens and a collimating mirror.

12. An arrangement for measuring a gas of interest by its optical absorption characteristics, said measuring arrangement comprising:
, a source of electromagnetic radiation;
means for directing such electromagnetic radiation through such gas of interest;
a first light signal, emerging from passage through such gas of interest, has associated therewith, periodic transmission spectra representative of the absorption lines of such gas of interest;
an interferometric device receptive of said first light signal and having associated therewith, a periodic spacing equal to the periodicity of the absorption lines of such gas of interest;
means for varying an applied electric field of first and second predetermined strengths to said interferometric device so as to modulate such periodic spacing of said interferometric device between transmission spectra which substantially coincide with such absorption lines and transmission spectra which fall between such absorption lines; and,
means for detecting at least an amount of such gas of interest as a function of the intensity of such periodic transmission spectra following passage through such gas of interest.

13. A measurement arrangement as set forth in claim 12 further comprising a sample cell in which such gas of interest is disposed, and a polarizer element disposed following said sample cell such that said light signal, after passing through such gas of interest, is polarized thereby in advance of said interferometric device.

14. A measurement arrangement as set forth in claim 12 further comprising means for conditioning said first light signal after it has passed through said interferometric device, said conditioning means being effective for removing preselected portions of said first light signal prior to said first light signal being acted upon by said detecting means.

15. A gas measurement arrangement as set forth in claim 12 wherein said interferometric device is a first birefringent etalon having a first path length determinative of such periodic spacing.

16. A gas measurement arrangement as set forth in claim 15 further comprising a second birefringent etalon disposed following said first birefringent etalon; said second birefringent etalon having a path length essentially twice that of said first birefringent etalon thereby having as a result thereof, an alternate periodic spacing associated therewith that is approximately one half that of said first birefringent etalon.

17. A gas measurement arrangement as set forth in claim 16 wherein said second birefringent etalon is disposed relative to said first birefringent etalon such that the respective periodic spacings of said first and second birefringent etalons are combined in a manner to yield a third periodic spacing which exhibits fewer and narrower absorption lines than such respective periodic spacings taken individually.

18. A method for measuring a gas of interest by its optical absorption characteristics, said measuring method comprising the steps of:
directing a light beam through a quantity of such gas of interest such that a light signal representative of the absorption lines of the gas of interest is generated thereby;
passing said light signal through a birefringent etalon device which has associated therewith, a periodic spacing substantially equivalent to such absorption lines associated with such gas of interest;
applying an electrical field at two distinct field strengths to the birefringent etalon to modulate its transmission spectra from wavelengths which substantially coincide with the absorption lines of the gas of interest and wavelengths which fall between such absorption liens; and
determining at least an amount of such gas of interest as a function of the relationship such spectra which coincide with such absorption lines and such spectra which fall between such absorption lines.

19. A gas measuring method as set forth in claim 18 further comprising the steps of: polarizing such light beam prior to said passing of such light beam through said birefringent etalon and conditioning such light beam after it has been modulated such that certain known portions of such light beam are removed prior to said amount determining step.

20. An arrangement for measuring a gas of interest by its optical absorption characteristics, said measuring arrangement comprising:
a source of electromagnetic radiation;
means for directing such electromagnetic radiation through such gas of interest;
a first light signal, emerging from passage through such gas of interest, has associated therewith, periodic transmission spectra representative of the absorption lines of such gas of interest;
means for modulating said first light signal between transmission spectra which substantially coincide with such absorption lines and transmission spectra which fall between such absorption lines;
an interferometric device receptive of said first light signal and having associated therewith a periodic spacing equal to the periodicity of the absorption liens of such gas of interest, said interferometric device further having associated therewith, a second periodic spacing substantially equivalent to such transmission spectra which fall between such absorption lines;
said interferometric device being shifted from said periodic spacing to said second periodic spacing by application of an electrical field thereto; and
means for detecting at least an amount of such gas of interest as a function of the intensity of such periodic transmission spectra following passage through such gas of interest.

21. A measurement arrangement as set forth in claim 20 wherein said interferometric device is a compound Fabry-Perot birefringent etalon device having associated therewith, a first index of refraction and a path length which determine, in conjunction, such periodic transmission spectra which substantially coincides with such absorption liens associated with such gas of interest.

22. A measurement arrangement as set forth in claim 21 wherein said birefringent etalon device further has associated therewith, a second index of refraction which determines such periodic transmission spectra which falls between such absorption lines associated with said gas of interest.

23. A measurement arrangement as set forth in claim 22 wherein said second index of refraction can be selected from a range of values such that such periodic transmission spectra which falls between such absorption lines associated with the gas of interest, occur at a wavelength which essentially avoids interference from gases other than such ga of interest.

24. A gas measurement arrangement as set forth in claim 21 wherein said birefringent etalon has applied on opposing ends disposed along the direction of light propagation through said gas measurement arrangement, a partially reflective surface coating, the amount of said surface coating being determinative of such reflectivity and further wherein, such reflectivity can be selectively varied so as to achieve varying degrees of finesse associated with said birefringent etalon.

* * * * *

UNITED STATES PATENT AND TRADEMARK OFFICE
CERTIFICATE OF CORRECTION

PATENT NO. : 4,998,017

DATED : March 5, 1991

INVENTOR(S) : Fredrick M. Ryan et al.

It is certified that error appears in the above-identified patent and that said Letters Patent is hereby corrected as shown below:

Col. 15, line 5, delete "ga", insert --gas--.

Signed and Sealed this

Twenty-first Day of July, 1992

Attest:

DOUGLAS B. COMER

Attesting Officer

Acting Commissioner of Patents and Trademarks